United States Patent [19]

Broberg et al.

[11] Patent Number: 4,529,601

[45] Date of Patent: Jul. 16, 1985

[54] LOCAL ANESTHETIC MIXTURE FOR TOPICAL APPLICATION AND METHOD FOR OBTAINING LOCAL ANESTHESIA

[75] Inventors: Berndt F. J. Broberg; Hans C. A. Evers, both of Södertälje, Sweden

[73] Assignee: Astra Lakemedel Aktiebolag, Sweden

[21] Appl. No.: 411,624

[22] Filed: Aug. 26, 1982

Related U.S. Application Data

[63] Continuation of Ser. No. 963,811, Nov. 27, 1978, abandoned.

[30] Foreign Application Priority Data

Dec. 1, 1977 [SE] Sweden .............................. 7713618

[51] Int. Cl.$^3$ .................... A61K 7/32; A61K 9/12; A61K 9/70; A61K 31/245
[52] U.S. Cl. ...................... 514/626; 424/28; 424/47; 424/65; 424/68; 514/817
[58] Field of Search ..................... 424/317, 168, 310

[56] References Cited

U.S. PATENT DOCUMENTS

| | | |
|---|---|---|
| 2,142,537 | 1/1939 | Tisza . |
| 2,175,782 | 10/1939 | Rorer . |
| 2,241,331 | 5/1941 | Shelton et al. . |
| 2,277,038 | 3/1942 | Curtis . |
| 2,286,718 | 6/1942 | Curtis . |
| 2,340,776 | 2/1944 | Stambovsky . |
| 2,352,691 | 6/1944 | Curtis . |
| 2,382,546 | 8/1945 | Curtis . |
| 2,395,538 | 2/1946 | Curtis . |
| 2,457,188 | 12/1948 | Stone . |
| 3,730,960 | 5/1973 | Wei et al. . |
| 3,751,562 | 8/1973 | Nichols . |
| 4,029,794 | 6/1977 | Adams et al. . |
| 4,046,886 | 9/1977 | Smith . |
| 4,091,090 | 5/1978 | Sipos . |

FOREIGN PATENT DOCUMENTS

| | | |
|---|---|---|
| 1299796 | 6/1960 | Fed. Rep. of Germany . |
| 306139 | 11/1968 | Sweden . |
| 889225 | 6/1960 | United Kingdom . |
| 1360820 | 7/1974 | United Kingdom . |

OTHER PUBLICATIONS

Chemical Abstracts, 1961, vol. 55, 10803-6, Rote Liste 1971, "Sprücaine Spray".

Primary Examiner—Dale R. Ore
Attorney, Agent, or Firm—Brumbaugh, Graves, Donohue & Raymond

[57] ABSTRACT

The present invention relates to pharmacological active preparations, especially local anesthetic preparations and deals with the problem of i a obtaining a solution of a local anesthetic agent in the form of its base, where the concentration is higher than otherwise possible. This problem has been dissolved according to the present invention thereby that one local anesthetic agent in the form of its base and as such having a melting point of 30° to 50° C., preferably prilocaine or tetracaine, is provided with one other local anesthetic agent in the form of its base and as such having a melting point of above 30° C., preferably above 40° C., preferably bensocaine, lidocaine, bupivacaine, mepivacaine, etidocaine or tetracaine which agents when brought and heated together form a homogenous oil having a melting of preferably below 40° C., more preferably below 25° C.

11 Claims, No Drawings

LOCAL ANESTHETIC MIXTURE FOR TOPICAL APPLICATION AND METHOD FOR OBTAINING LOCAL ANESTHESIA

This is a continuation of application Ser. No. 963,811, filed Nov. 27, 1978, now abandoned.

The present invention relates to a mixture of local anesthetically active compounds in base form in order to obtain topical anesthesia through skin, process for its preparation, and method for obtaining topical local anesthesia.

The object of the present invention is to obtain a possibility of utilizing local anesthetically active compounds in base form and to obtain a maximal concentration of active substance at the application on skin in order to obtain local anesthesia with as low a dose as can be.

It is previously known, e.g. by Swedish Patent S/No. 352 239 to produce a local anesthetically active film comprising lidocaine in crystallized, microdisperse form. The film is hereby intended to be used for anesthesia of mucous membranes, especially in the mouth cavity for blocking the nerves around the teeth in order to facilitate smaller incisions. Lidocaine is present in the film in 2 to 40% by weight. The drawback of said solid carrier is that an exactly adjusted dose can not be obtained to penetrate as one can not judge in the single case how much of lidocaine is left in the film carrier. The concentration of lidocaine can as easily understood, neither become so high, which results in that higher doses than necessary must be used.

It is further known to combine two or more local anesthetics in the form of acid addition salts in aqueous solutions for injection. (Cf British Patent Specification S/No. 1 360 820). In such case the active agents are present in watersoluble form and do not form a homogenous oil.

Previously, the problem has also been to utilize local anesthetically active compounds in the form of their bases as these are in crystalline form at room temperature and acceptable effect is not obtained when the substance is applied in crystalline form.

The wish has than been to obtain an oil phase, containing high amount of local anesthetic, which, by means of a simple carrier, easily can be applied on the intended surface.

It has now surprisingly been found that it is possible to obtain such a form by means of the present invention, whereby moreover, a more deep penetrative effect as well as an improved local anesthesia is obtained, whereby the invention is characterized in that one local anesthetic agent in the form of its base and as such having a melting point of 30° to 50° C. is mixed with one other local anesthetic agent in the form of its base and as such having a melting point of above 30° C., preferably above 40° C.

According to a preferred embodiment of the invention prilocaine or tetracaine in base form is mixed with one of benzocaine, lidocaine, bupivacaine, mepivacaine, or etidocaine or tetracaine in base form. It is evident that when tetracaine is used as first base it can not be used as second base.

According to a preferred embodiment prilocaine and bensocaine are mixed in a weight ratio of 65:35 to 80:20, preferably 70:30.

According to a preferred embodiment prilocaine and lidocaine are mixed in a weight ratio of 42:58 to 80:20, preferably 47:53 to 62:38.

According to another preferred embodiment prilocaine and etidocaine are mixed in a weight ratio of 55:45 to 95:5, preferably 60:40 to 80:20.

According to a further preferred embodiment prilocaine and mepivacaine are mixed in a weight ratio of 80:20 to 97:3, preferably 85:15 to 90:10.

According to another, further preferred embodiment prilocaine and bupivacaine are mixed in a weight ratio of 72:28 to 97:3, preferably 78:22 to 88:12.

According to another preferred embodiment of the invention tetracaine and lidocaine in their base forms are mixed in a weight ratio of 40:60 to 70:30, preferably 45:55 to 55:45, most preferably 50:50.

In accordance with the invention (a) a local anesthetic agent in the form of its base is mixed with (b) one other local anesthetic agent in the form of its base, whereby the agent under (a) has a melting point of 30° to 50° C. and the agent under (b) has a melting point of above 30° C. preferably above 40° C.

Compounds under (a) are prilocaine, tetracaine, butanilicaine and trimecaine.

Compounds under (b) are bensocaine, lidocaine, bupivacaine, dibucaine, mepivacaine and etidocaine, as well as tetracaine, butanilicaine and trimecaine.

When the local anesthetic agents of (a) and (b) respectively in base, crystalline form are mixed together and heated the mixture shall have a resulting melting temperature of below 40° C. and thereby form a homogenous oil. The oil is completely reformed if heated to the melting point even after a storage at low temperature for long time.

The above given weight ratios give mixtures which melt at temperatures below 40° C. and are present in the form of an oil.

According to another aspect of the present invention a method for obtaining local anesthesia by means of topical application on skin, whereby a mixture of prilocaine or tetracaine in the form of its base, and any of the compounds ensocaine, lidocaine, bupivacaine, mepivacaine, etidocaine or tetracaine in a therapeutically effective amount is applied onto the skin surface through which anesthesia is to be obtained.

According to a preferred embodiment the mixture is added in a dose of 0.5 to 10 mg/cm$^2$ of skin.

The expression skin above relates to mucous membrane as well as intact or wounded skin.

According to another aspect of the invention injectable compositions are obtained, which injectable compositions contain in oil form one local anesthetic agent in base form and as such having a melting point of 30° to 50° C., and one other local anesthetic agent in base form and as such having a melting point of above 30° C., preferably above 40° C.

Such a composition will have a potent clinical use in more rapid onset of effect and/or prolonged duration of local anesthetic effect.

Above given compounds except for bensocaine and tetracaine are represented by the general formula

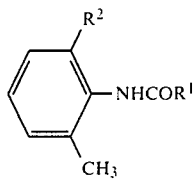

wherein $R^1$ is

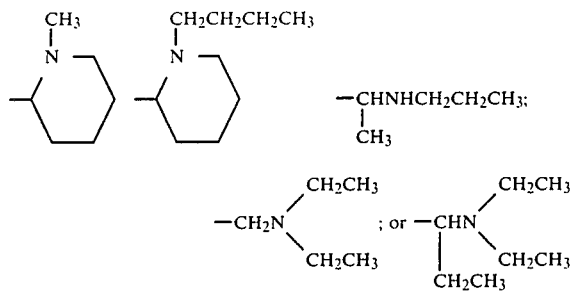

and $R^2$ is hydrogen or methyl, whereby $R^2$ is hydrogen when $R^1$ is

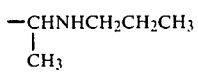

Bensocaine, 4-aminobenzoic acid ethyl ester, has the formula

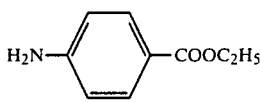

Tetracaine, 2-(dimethylamino)ethylester of p-butylaminobensoic acid has the formula

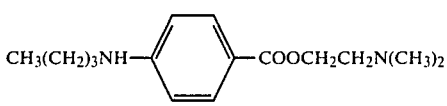

1-methyl-2-(2,6-xylylcarbamoyl)piperidine is known under the generic name mepivacaine and is sold under the trade mark Carbocaine ®.

1-butyl-2-(2,6-cylylcarbamoyl)piperidine is known under the generic name bupivacaine and is sold under the trade mark Marcaine ®.

2-propylamino-N-(2-tolyl)propionamide is known under the generic name prilocaine and is sold under the trade mark Citanest ®.

Diethylaminoacet-2,6-xylidide is known under the generic name lidocaine and is sold under the trade mark Xylocaine ®.

2-ethylpropylamino-2,6-n-butyroxylidide is known under the generic name etidocaine and is sold under the trade mark Duranest ®.

Prilocaine has a melting point of 38° C.: lidocaine a melting point of 68° C.; etidocaine a melting point of 88° C.; mepivacaine a melting point of 155° C.; bupivacaine a melting point of 110° C.; bensocaine a melting point of 89° C., tetracaine a melting point of 41° C., butanilicaine a melting point of 45°–46° C., trimecaine a melting point of 44° C., and dibucaine a melting point of 65° C.

Above given mixtures have a melting point minimum within the given ranges. The mixtures form eutectic mixtures, with eutectic minima.

The oil formed by the local anesthetically active compounds in the form of their bases can be administered as such, or be transferred onto a carrier such as paper, or be introduced into a liquid carrier in order to form an emulsion, or as an emulsion in an ointment base. The different forms of preparation, depend on where one wants to obtain anesthesia.

After anesthesia through the skin the following incisions can be made.

Mucous membrane: the taking of a punch biopsy, smaller incisions in underlying mucous membrane, eg curettage, or gingivectomi or tooth tartar removal, elimination of needle prick pain at an injection. Otholaryngological incisions in nose and throat, eg biopsy or trepanation.

Paracentesis of drum-membrane.

Sample excision in the urogenitalic area.

Local anesthesia of cervix at delivery.

Intact skin: Smaller cutaneous incisions eg biopsy, or excision of naevi, elimination of needle prick pain before injection.

The present invention will in the following be described more in detail with reference to a number of examples.

EXAMPLE 1

| | |
|---|---|
| Prilocaine, base | 52 g |
| Lidocaine, base | 48 g |
| | 100 g |

The two local anesthetically active compounds in crystalline form were weighed together and heated to 30° C., whereby the two compounds melted and formed a homogenous oil. The mixture of crystals has a melting point of 22° C. The mixture did not crystallize even for very long time of storage at strong cold, when reheated to 22° C.

EXAMPLE 2

| | |
|---|---|
| Prilocaine, base | 70 g |
| Etidocaine, base | 30 g |
| | 100 g |

The two local anesthetically active compounds, in crystalline form, were weighed together and were treated to 35° C., whereby the two compounds melted and formed a homogenous oil. The melting point of the mixture is 29° C.

EXAMPLE 3

| | |
|---|---|
| Prilocaine, base | 85 g |
| Mepivacaine, base | 15 g |
| | 100 g |

The two local anesthetically active compounds in crystalline form, were weighed together and were heated to 40° C., whereby the two compounds melted and formed a homogenous oil. The melting point of the mixture is 33° C.

EXAMPLE 4

| Prilocaine, base | 80 g |
|---|---|
| Bupivacaine, base | 20 g |
| | 100 g |

The two local anesthetically active compounds, in crystalline form, were weighed together and heated to 40° C., whereby the compounds melted and formed a homogenous oil. The melting point of the mixture is 34° C.

EXAMPLE 5

| Prilocaine, base | 70 g |
|---|---|
| Bensocaine, base | 30 g |
| | 100 g |

The two local anesthetically active compounds, in crystalline form, were weighed together and were heated to 35° C., whereby the compounds melted and formed a homogenous oil. The melting point is 29° C.

EXAMPLE 6

| Tetracaine, base | 50 g |
|---|---|
| Lidocaine, base | 50 g |
| | 100 g |

The two local anesthetically active compounds, in crystalline form, were mixed together and were then heated to 25° C., whereby the compounds melted and formed an homogenous oil. The melting point of the mixture is 17° C.

EXAMPLE 7

A mixture according to Example 1 was applied onto a carrier of paper in an amount of 1.5 mg/cm$^2$. The carrier, 1 cm$^2$, with the mixture was applied on the teeth gums in the vicinity of the root point of the tooth to be treated, prior to a deep cavity preparation in a vital tooth. After about 5 min the treatment could be carried out without giving the patient any pain sense.

Lidocaine and prilocaine alone do not give such an anesthetic effect.

The mixtures prepared shall preferably be present in oil form at temperatures about 40° C. and below.

Biological Effect

The biological effect of the local anesthetic mixture of the present invention was determined in an experimental investigation of dermal analgesia by epidermal application of different local anesthetic formulations.

In the present investigation it was shown in 12 volunteers that the pain response, induced by pin-pricking, was partly blocked by epidermal application of different local anaesthetic formulations. Dermal analgesia (tested by pin-pricking) was most pronounced with a formulation consisting of a eutectic mixture of lidocaine base and prilocaine base, in a total concentration of 10%, as an aqueous emulsion. The other two tested formulations, containing 10% lidocaine and 10% prilocaine base respectively, were less effective, with regard to dermal analgesia, even if these produced some demostrable effects, different from a placebo emulsion.

Material and Method 12 healthy medical students from the Uppsala University Hospital took part in the study.

Pre-formed pads, consisting of cellulose fibres, 2 times 2 centimeters, were soaked by a standardized procedure in either an emulsion containing 5% lidocaine base+5% prilocaine base, an emulsifying agent and water, 10% lidocaine base in the same vehicle, 10% prilocaine base in the same vehicle, or a placebo emulsion containing the emulsifying agent and water only. On one forearm of the volunteer the four different emulsions were applied under occlusive dressings consisting of impervious tape, while on the other arm the four emulsions were applied under a non-occlusive dressing, using surgical tape (3M). A certain distance between the application areas was chosen in order to avoid any risk of interference between them.

On the arms of the volunters 11 and 12 the emulsions were applied directly to the skin, with no cellulose pads, but with occlusive and non-occlusive dressings applied as in the other volunteers.

The application time for the pads was 60 minutes.

Immediately after removal of the pads, the square areas under the two types of dressing were marked at the edges. A line was also marked within each applied area dividing them into two identical triangles. One of these surfaces were then used for the pin-prick experiments, the other for studying other effects.

Testing of Dermal Analgesia

The pin-pricking procedure was carried out with disposable dental needles. In each of the test areas 10 pin-pricks were made. 10/10 represents full analgesia, 0/10 no analgesia.

Results

The lidocaine-prilocaine emulsion was found to be significantly more effective than the lidocaine emulsion, the prilocaine emulsion and the placebo emulsion in producing dermal analgesia. By the student's t-toT test it was found that:

| | |
|---|---|
| Lidocaine-prilocaine versus placebo: p = 0.001 | Under |
| Lidocaine-prilocaine versus lidocaine: p = 0.001 | occlusive |
| Lidocaine-prilocaine versus prilocaine: p = 0.01 | bandage |
| Lidocaine-prilocaine versus placebo: p = 0.01 | Under non- |
| Lidocaine-prilocaine versus lidocaine: p = 0.01 | occlusive |
| Lidocaine-prilocaine versus prilocaine: p = 0.01 | bandage |

The lidocaine and prilocaine emulsions were found to be insignificantly more effective than the placebo emulsion under occlusion as well as insignificantly different in effect to placebo under a non-occlusive bandage, as evident from Table I, statistical data, below.

TABLE I

| | Pin-prick | | | | | | | |
|---|---|---|---|---|---|---|---|---|
| | Occlusion | | | | Non-occlusion | | | |
| | L-P | L | P | Placebo | L-P | L | P | Placebo[1] |
| 1 | 10/10 | 2/10 | 0/10 | 0/10 | 7/10 | 0/10 | 0/10 | 0/10 |
| 2 | 10/10 | 0/10 | 0/10 | 0/10 | 10/10 | 0/10 | 0/10 | 0/10 |
| 3 | 2/10 | 0/10 | 0/10 | 0/10 | 0/10 | 0/10 | 0/10 | 0/10 |
| 4 | 10/10 | 5/10 | 10/10 | 0/10 | 10/10 | 0/10 | 6/10 | 0/10 |

TABLE I-continued

| | | | | | | | | |
|---|---|---|---|---|---|---|---|---|
| 5 | 9/10 | 3/10 | 1/10 | 0/10 | 7/10 | 1/10 | 0/10 | 0/10 |
| 6 | 8/10 | 2/10 | 0/10 | 0/10 | 9/10 | 0/10 | 0/10 | 0/10 |
| 7 | 8/10 | 0/10 | — | 0/10 | 2/10 | 0/10 | 1/10 | 0/10 |
| 8 | 10/10 | 0/10 | 2/10 | 0/10 | 8/10 | 0/10 | 0/10 | 0/10 |
| 9 | 7/10 | 2/10 | 0/10 | 4/10 | 0/10 | 0/10 | 0/10 | 0/10 |
| 10 | 0/10 | 0/10 | 0/10 | 0/10 | 0/10 | 0/10 | 0/10 | 2/10 |
| $M_{1-10}$ | 7.40 | 1.40 | 1.44 | 0.40 | 5.10 | 0.10 | 0.70 | 0.20 |
| 11 | 10/10 | 8/10 | 7/10 | 0/10 | 5/10 | 0/10 | 2/10 | 0/10 |
| 12 | 10/10 | 6/10 | 9/10 | 0/10 | 3/10 | 0/10 | 0/10 | 0/10 |
| $M_{1-12}$ | 7.82 | 2.33 | 2.64 | 0.30 | 4.92 | 0.08 | 0.75 | 0.17 |

Statistical data

Patients No.

| | | |
|---|---|---|
| 1–10 | L-P/placebo: t = 5.78*** | L-P/placebo: t = 3.40** |
| | L-P/L: t = 5.87*** | L-P/L: t = 3.70** |
| | L-P/P: t = 11.33** | L-P/P: t = 3.50** |
| 1–12 | L-P/placebo: t = 7.11*** | L-P/placebo: t = 3.96** |
| | L-P/L: t = 6.03*** | L-P/L: t = 4.29** |
| | L-P/P: t = 4.30** | L-P/P: t = 3.97** |

Pin-Prick

Occlusion

Patients No

| | |
|---|---|
| 1–10 | L/placebo: t = 1.58 n s |
| | P/placebo: t = 0.80 n s |
| 1–12 | L/placebo: t = 2.32* |
| | P/placebo: t = 1.71 n s |

Non-occlusion

| | |
|---|---|
| 1–10 | L/placebo: t = 0.42 n s |
| | P/placebo: t = 0.76 n s |
| 1–12 | L/placebo: t = 0.43 n s |
| | P/placebo: t = 1.05 n s |

[1] L-P = lidocaine-prilocaine comp
L = lidocaine comp
P = prilocaine comp

It has also been shown that the present combinations of local anesthetics possess worthwhile properties in inhibiting perspiration. They can thus be used in antiperspirant compositions as emulsions for roll-on, or emulsions or solutions for spraying.

We claim:

1. A locally active anesthetic agent in the form of a homogenous oil which is useful for topical or parenteral application, consisting essentially of prilocaine in the form of its base in admixture with lidocaine, in the form of its base in a weight ratio of 42:58 to 80:20 such that the resulting mixture is a homogenous oil which has a melting point of below 40° C.

2. An agent according to claim 1, characterized in that the mixture has a melting point below 25° C.

3. An agent according to claim 1, wherein the weight ratio is 47:53 to 62:38.

4. An agent according to claim 3, wherein the weight ratio is 55:45.

5. An agent according to claim 3, wherein the weight ratio is 52:48.

6. An agent according to claim 3, wherein the weight ratio is 50:50 and the preparation also contains an emulsifying agent.

7. A method of obtaining local anesthesia in mammals by way of topical or parenteral application, which comprises administering an anesthetically effective amount of a combination of prilocaine in the form of its base in admixture with lidocaine in the form of its base in a weight ratio of 42:58 to 80:20 such that the resulting mixture is a homogenous oil which has a melting point of below 40° C.

8. A method of obtaining local anesthesia in mammals as described in claim 7, wherein the weight ratio is 47:53 to 62:38.

9. A method of obtaining local anesthesia in mammals as described in claim 8, wherein the weight ratio is 55:45.

10. A method of obtaining local anesthesia in mammals as described in claim 8, wherein the weight ratio is 52:48.

11. A method of obtaining local anesthesia in mammals as described in claim 8, wherein the weight ratio is 50:50 and the combination also contains an emulsifying agent.

* * * * *